United States Patent
Pratt

(10) Patent No.: US 6,601,889 B2
(45) Date of Patent: Aug. 5, 2003

(54) AIR-TIGHT BAILER SYSTEM

(76) Inventor: David W. Pratt, 13512 Feather Sound Cir. West, Apt. 1401, Clearwater, FL (US) 33760

( * ) Notice: Subject to any disclaimer, the term of this patent is extended or adjusted under 35 U.S.C. 154(b) by 5 days.

(21) Appl. No.: 09/682,845

(22) Filed: Oct. 24, 2001

(65) Prior Publication Data

US 2003/0075940 A1 Apr. 24, 2003

(51) Int. Cl.$^7$ .............................. G01N 1/12; E21B 31/08
(52) U.S. Cl. ................................ 294/68.25; 73/864.63; 166/162; 215/355; 220/256.1
(58) Field of Search .......................... 294/68.25, 68.22, 294/82.11, 86.1–86.3; 166/66, 66.6, 66.7, 99, 162, 165, 332.8, 167; 73/864.63, 864.91; 206/524.8; 383/41; 215/306, 355, 356; 220/255, 256.1, 375, DIG. 19

(56) References Cited

U.S. PATENT DOCUMENTS

| | | | | |
|---|---|---|---|---|
| 300,240 A | * | 6/1884 | Foat | 294/68.25 |
| 2,059,999 A | * | 11/1936 | Rainville, Sr. | 73/864.63 |
| 2,987,175 A | * | 6/1961 | Bottum | 215/355 |
| 4,174,424 A | * | 11/1979 | Jurva et al. | 220/256.1 |
| 4,625,574 A | * | 12/1986 | Robbins | 73/864.63 |
| 4,845,038 A | * | 7/1989 | Barr et al. | 215/354 |
| 4,953,728 A | * | 9/1990 | Meek | 215/355 |
| 4,974,744 A | * | 12/1990 | Shanklin et al. | 220/254.1 |
| 5,341,692 A | * | 8/1994 | Sher et al. | 73/864.63 |
| 5,349,875 A | * | 9/1994 | Sher et al. | 73/864.65 |
| 5,454,275 A | * | 10/1995 | Kabis | 166/162 |
| 5,494,170 A | * | 2/1996 | Burns | 215/247 |
| 5,537,881 A | * | 7/1996 | White | 73/864.63 |
| 5,597,966 A | * | 1/1997 | Timmons | 73/864.63 |
| 5,699,923 A | * | 12/1997 | Burns | 215/355 |
| 6,196,074 B1 | * | 3/2001 | Varhol | 73/863.23 |
| 6,276,220 B1 | * | 8/2001 | Varhol | 73/864.51 |
| 6,431,272 B1 | * | 8/2002 | Pratt | 166/162 |
| 2002/0185878 A1 | * | 12/2002 | Pratt | 294/68.25 |

* cited by examiner

*Primary Examiner*—Eileen D. Lillis
*Assistant Examiner*—Paul T. Chin
(74) *Attorney, Agent, or Firm*—Ronald E. Smith; Smith & Hopen, P.A.

(57) ABSTRACT

An air-tight bailer is filled completely and closed at its open upper end with a flat cap so that no ambient air is trapped in the bailer. A mounting member to which a rope is secured for lowering and lifting the bailer is recessed with respect to the open upper end of the bailer so that it does not interfere with the cap. A disc-shaped protuberance formed on the bottom of the cap fills the recess. An annular groove around the recess receives the rim of the open upper end to enhance an air-tight seal between the cap and the open upper end. In a first embodiment, the bailer is emptied by piercing a thin membrane formed in the cap with a spout device having a trailing end in fluid communication with a container. A second embodiment eliminates the membrane and the spout device.

14 Claims, 4 Drawing Sheets

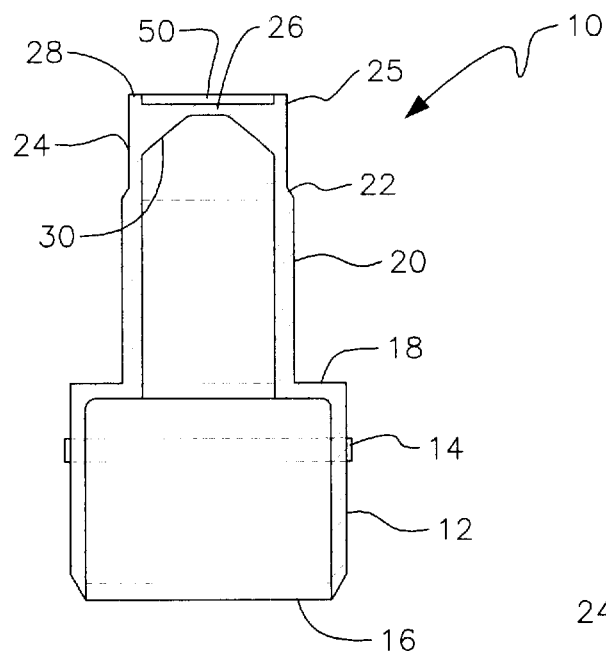
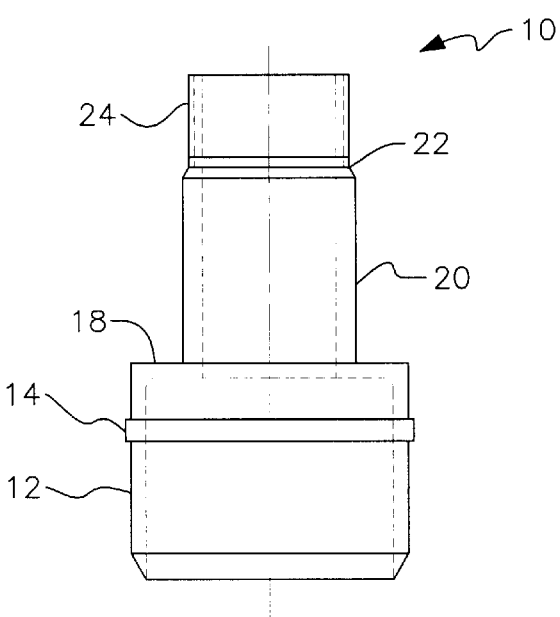
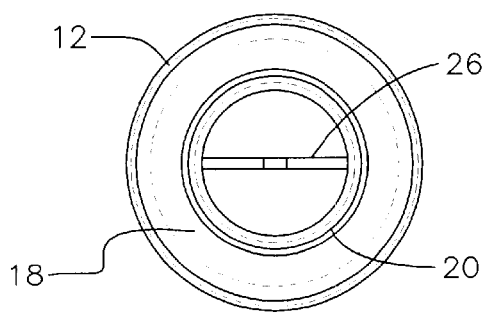

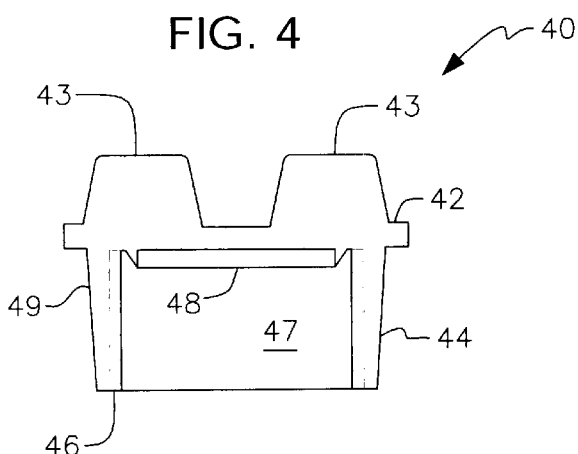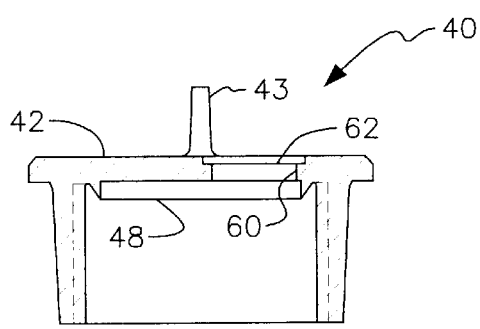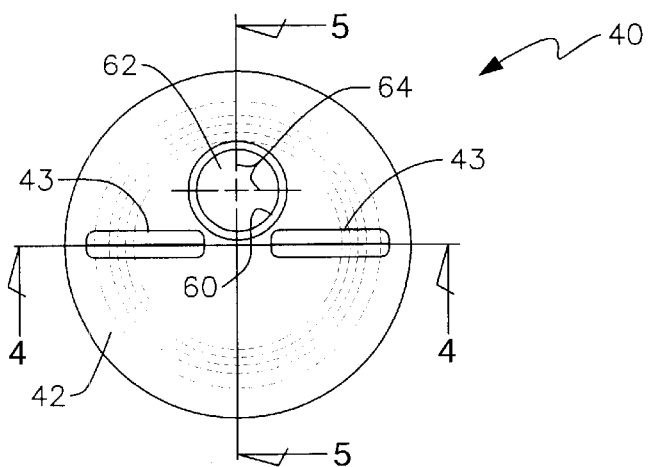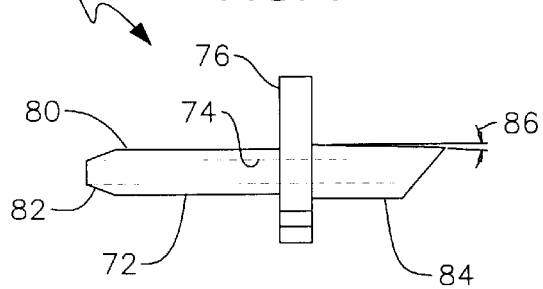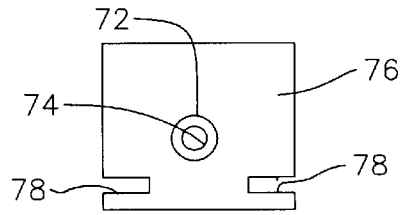

AIR-TIGHT BAILER SYSTEM

BACKGROUND OF INVENTION

1. Field of the Invention

This invention relates, generally, to bailers. More particularly, it relates to a bailer system that minimizes contamination of a liquid sample by oxygen or other gases present in ambient air.

2. Description of the Prior Art

The purpose of a bailer is to collect a liquid sample from a body of liquid fluid, such as a well, and to enable the collected sample to be delivered to a lab in the substantial absence of contamination of the sample by substances that were not present in the well when the sample was collected.

However, every known bailer allows air to contact the liquid sample after the bailer has been retrieved from a well. Oxygen in the air dissolves into the sample, contaminating it and causing a lab charged with determining the chemical make-up of the sample to produce inaccurate reports.

Many bailers are open-topped and are emptied into lab-bound containers by inverting the bailer. Such a decanting procedure allows oxygen contamination to occur.

Many bailers are emptied from the bottom by an emptying device known in the industry as a V.O.C. device. Such a device lifts a check valve at the bottom of a bailer from its valve seat so that the contents of the bailer are free to flow into a container that will be shipped to a lab. Like top-pouring, this decanting technique also allows atmospheric air to freely contact the liquid sample.

Recently, the present inventor developed an improved bailer designed to minimize contamination of the collected sample. Instead of emptying a bailer into a container, the bailer is capped at its opposite ends as soon as it is retrieved from the well. In this way, the bailer serves a dual function that of a bailer and as a container suitable for shipment to a lab. By capping the opposite ends of a full bailer, the interaction of the liquid sample and atmospheric air caused by transferring the bailer contents to a container by pouring or by use of a V.O.C. device is avoided.

However, an air bubble remains within the capped bailer because such bubble is trapped within the bailer at the time the bailer is capped. The bailer cap invented by the present inventor has a top wall and cylindrical sidewalls mounted about the periphery of the top wall in depending relation thereto. Internal screw threads are formed on an interior surface of the cylindrical sidewalls and such screw threads releasably engage external screw threads formed in the uppermost end of the bailer. The hollow cavity formed by the top wall and the cylindrical sidewalls therefore traps a small volume of air when the cap is placed onto the bailer. The hollow cavity is required to accommodate the handle or mounting means of the bailer, said mounting means having a rope or similar flexible lifting and lowering means tied thereto.

What is needed, then, is a bailer that substantially prevents air from coming into contact with the contents of the bailer. Such a bailer would enable a laboratory to test liquid fluid from a bailer that has not been contaminated by contact with atmospheric air.

More particularly, there exists a need for a bailer that traps no air bubbles therewithin when the bailer is capped for shipment to a lab.

However, in view of the prior art considered as a whole at the time the present invention was made, it was not obvious to those of ordinary skill in the pertinent art how the identified need could be fulfilled.

SUMMARY OF INVENTION

The longstanding but heretofore unfulfilled need for an air-tight bailer is now met by a new, useful, and nonobvious invention that provides a complete system for collecting liquid fluids in the field and delivering said liquid fluids to a laboratory in an uncontaminated state.

The novel bailer system includes a top piece adapted to engage a main body of the bailer. The top piece has an open upper end of predetermined diameter. A mounting member adapted to be engaged by a rope means for lowering and lifting the bailer into and out of a body of liquid fluid is disposed in spanning relation to the open upper end of the top piece. Significantly, the mounting member does not extend above the plane of the open upper end so that it does not interfere with a novel closure means.

The novel closure means is provided for closing the open upper end when the bailer is full of liquid fluid. The closure means has a flat base that overlies the open upper end and has sidewalls depending from the flat base that are adapted to engage an external surface of the top piece. In this way, the closure means is secured to the top piece when the bailer is completely filled with liquid fluid so that no air is trapped within the bailer.

In a first embodiment, the closure means further includes a pair of guide plates formed integrally with the flat base wall that project upwardly therefrom. Each guide plate has a flat structure and is positioned on a diameter of the top wall in diametrically opposed relation to its counterpart guide plate.

A spout means in the form of a tube has a leading end adapted for penetrating the flat top wall of the closure means and a trailing end adapted for connection to a hose means that is in fluid communication with a laboratory container adapted to receive the sampled liquid fluid. Thus, liquid fluid within the bailer may flow through the spout means and through the hose means into the laboratory container when the leading end of the spout means penetrates the flat top wall and the bailer is inclined to provide a gravity feed.

A transverse plate of flat configuration is mounted transversely to a longitudinal axis of the spout means and a pair of slots is formed therein. Each slot has its outermost end in open communication with an edge of the transverse plate and is adapted to slidingly engage an associated closure means guide plate.

An opening is formed in the flat top wall of the closure means and an imperforate membrane covers the opening so that no liquid fluid may flow therethrough. The leading end of the spout means is adapted to penetrate the membrane. The user positions the spout means in the center of the membrane by slidingly interconnecting the slots of the transverse plate to the guide plates of the closure means.

In a second embodiment, the spout means, the transverse plate, and the membrane are obviated. Instead, an upstanding tubular spout is formed in the top wall of the closure means in diametrically opposed relation to an upstanding post. A flexible, elongate closure means has a first end secured to the post and a second imperforate end adapted to releaseably engage and seal the upstanding tubular spout.

When the first embodiment is used, a user manually squeezes a filled bailer so that the bailer overflows at its uppermost end. This ensures that all air bubbles have been removed from the hollow interior of the bailer. The novel closure means of the first embodiment is then secured to the uppermost end of the bailer to ensure that no air enters into the bailer when the squeezing action is terminated.

When the second embodiment is used, a user squeezes a filled bailer until the liquid fluid in the hollow interior of the bailer overflows the upstanding tube formed in the closure means. The free end of the flexible, elongate closure means is then brought into sealing relation to the tubular spout to ensure that no air can enter the bailer when the squeezing action is terminated.

An important object of this invention is to provide an air-tight bailer so that a laboratory test of oxygen content of a collected sample will not be contaminated with oxygen from the ambient environment.

A closely related object is to enable transfer of the contents of a full bailer to a laboratory container without allowing ambient air to contact the sampled liquid fluid as it is being transferred.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which:

FIG. 1 is a front elevational view of the novel top end piece of a bailer;

FIG. 2 is a side elevational view thereof;

FIG. 3 is a top plan view thereof;

FIG. 4 is a sectional view of a novel closure means taken along line 4—4 in FIG. 6;

FIG. 5 is a sectional view taken along line 5—5 in FIG. 6;

FIG. 6 is a top plan view of said novel closure means;

FIG. 7 is a side elevational view of the novel spout;

FIG. 8 is a top plan view of said spout;

DETAILED DESCRIPTION

Figure 9:
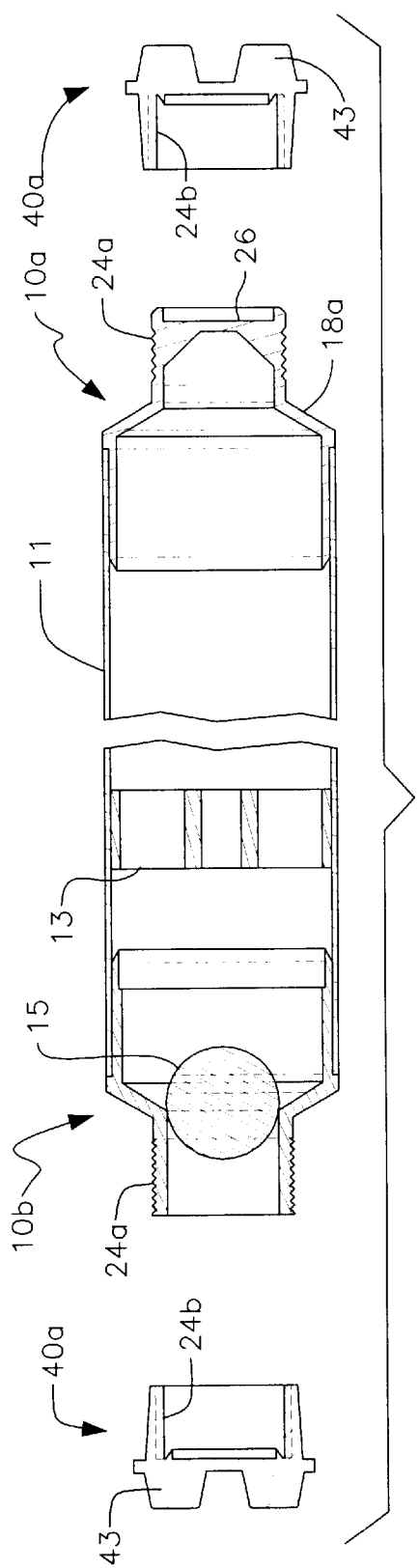
FIG. 9 is an exploded, broken longitudinal sectional view of a bailer.

Referring to FIGS. 1 and 2, it will there be seen that the reference numeral 10 denotes an illustrative embodiment of the present invention as a whole.

Element 10 is a top piece that surmounts a conventional bailer, not shown in FIGS. 1 and 2. Lower cylindrical sidewalls 12 are slidingly inserted into the uppermost end of the main cylindrical body of a bailer, i.e., into the hollow interior of said bailer. Accordingly, the exterior diameter of sidewalls 12 is slightly less than the interior diameter of the bailer to ensure a snug fit. Adhesive is used to ensure an airtight fit.

Annular ridge 14 circumscribes sidewalls 12 at a preselected height above the bottom edge 16 thereof to limit the depth of insertion.

Annular shoulder 18 reduces the diameter of top piece 10 so that the exterior diameter of upper cylindrical sidewalls 20 is less than that of the lower cylindrical sidewalls 12 as depicted. It should be understood that this reduction in diameter is for the purpose of saving materials. The invention disclosed herein works even if diameter-reducing shoulder 18 is not provided.

Annular bevel 22 reduces the diameter of upper cylindrical sidewalls 20 by a small amount as depicted, so that uppermost cylindrical sidewalls 24 have an external diameter only slightly less than the external diameter of upper cylindrical sidewalls 20.

As perhaps best understood by comparing FIGS. 1 and 2 with FIG. 3, mounting means 26 has a straight configuration and is diametrically disposed with respect to the interior diameter of uppermost cylindrical sidewalls 24. A careful inspection of FIG. 1 indicates that mounting means 26 is slightly recessed from uppermost edge 28 of said sidewalls 24. The short extent of sidewalls 24 that extends above the plane of mounting means 26 is denoted 25 in FIG. 1 and will hereinafter be referred to as the rim of top piece 10. The area circumscribed by rim 25, i.e., the area above the plane of mounting means 26 and below top edge 28 of top piece 10 is referred to hereinafter as recess 50.

As may also be seen in FIG. 1, a pair of wedge-shaped braces, collectively denoted 30, are formed in opposite ends of said mounting means 26. Braces 30 perform the function their name expresses.

When a bailer is lowered into or lifted from a well or other reservoir of liquid fluid, a string, rope, cable, or similar connecting means is tied or otherwise secured to mounting means 26. It is critical to this invention that said mounting means does not project above upper edge 28 of uppermost cylindrical walls 24. In prior art bailers, the mounting means projects above the uppermost edge of the cylindrical main body of the bailer, or above the uppermost edge of a top piece connected to said main body. Accordingly, if a cap is employed to close the upper end of a prior art bailer, the cap must have a hollow interior to accommodate the upwardly-projecting mounting means. Thus, air in the cap is trapped within the hollow interior of the cap and hence is trapped within the hollow interior of a bailer when such a cap is mounted to the bailer. No such cap is required in the present invention because mounting means 26 does not extend above uppermost edge 28.

A closure means particularly adapted to close the upper open end of top piece 10 is denoted as a whole by the reference numeral 40 in FIGS. 4–6. As best understood by comparing those three Figures with one another, closure means 40 has a disc-shaped base 42. A pair of upstanding, flat guide members, collectively denoted 43, is formed integrally with base 42 and projects upwardly therefrom as depicted. Guide members 43 are formed on a diameter of base 42 in diametrically spaced apart relation to one another.

Cylindrical sidewalls 44 are also integrally formed with base 42 and depend therefrom as depicted. The longitudinal extend of sidewalls 44 is preselected so that the lowermost edge 46 of said sidewalls abuts annular bevel 22 of top piece 10. Cavity 47 is defined by the structure of closure means 40.

A disc-shaped insert or protuberance 48 of shallow depth is formed integrally with and depends from base 42 and has a diameter slightly less than the interior diameter of cylindrical sidewalls 44 as depicted. That structure creates an annular groove 49 that circumscribes protuberance 48.

When closure means 40 closes top piece 10, protuberance 48 is slideably received within and fits snugly within recess 50 in FIG. 1. Diametrically disposed mounting means 26 defines the lowermost boundary of area 50 and the edge of sidewall 24 that projects above the plane of said mounting means 26, denoted 25 as aforesaid, defines the annular boundary of said recess 50. Thus, when closure means 40 (FIGS. 4–6) is disposed in closing relation to top piece 10 (FIGS. 1–3), sidewalls 24 of top piece 10 are received within cavity 47 of closure means 40 in snug, sliding relation to the interior surface of sidewalls 44. Rim 25 of top piece 10 fits into and fully occupies annular groove 49 when closure means 40 is fully seated on top piece 10. Accordingly, if the bailer is completely full, i.e., if liquid fluid extends to top edge 28 of top piece 10, no air pockets will be formed and hence no air will be trapped in the bailer or cap 40 when said cap 40 is fully seated on top piece 10.

If the bailer is not completely full, it is squeezed by hand until the level of liquid fluid therewithin rises to a height where it is flush with said top edge 28. As a practical matter, the bailer is squeezed until the liquid fluid in the hollow interior thereof slightly overflows top edge 28. Closure means 40 is then attached to top piece 10 and no air bubbles are present in the liquid fluid when the squeezing action is terminated because the seal between cap 40 and top piece 10 is air-tight.

As perhaps best indicated in FIG. 5, the means for emptying the air-tight bailer includes an aperture 60 formed in base 42. Note that aperture 63 does not extend all of the way through said base 42. A thin membrane 62, flush with the top surface of base 42, closes said aperture 60 and thus seals the bailer. A pair of score lines, collectively denoted 64 in FIG. 6, is formed in said membrane 62 to weaken it. Score lines 64 do not extend through membrane 62 and thus are not a source of leakage.

FIGS. 7 and 8 depict the novel V.O.C. member that serves as a spout when the bailer is transferred to a laboratory container in a laboratory. Spout 70 has a tubular main body 72 that defines lumen 74 through which liquid fluid flows when the bailer is emptied. Flat plate 76 is mounted transversely to a longitudinal axis of tube 72 and is secured thereto by suitable means so that it does not slip along the length of said tube 72. It is hereinafter referred to as transverse plate 76. A pair of slots, collectively denoted 78, are formed in transverse plate 76 and their respective outermost ends are in open communication with their respective plate edges as depicted.

The trailing end of spout 70 is denoted 80 and has an annular bevel 82 formed therein to facilitate connection of a tube, not shown, to said trailing end. The unillustrated tube provides fluid communication from spout 70 to a laboratory container, not shown.

The leading end of spout 70 is denoted 84. The draft angle denoted 86 is about five degrees (5°).

To use V.O.C. device 70, slots 78 are aligned with guide plates 43 and leading end 84 of device 70 is pressed against score lines 64 until membrane 62 gives way. Guide plates 43, 43 serve to properly position leading end 84 in proper puncturing relation to score lines 64. Draft angle 86 prevents said leading end from getting stuck in opening 60 when membrane 62 breaks.

FIG. 9 depicts top piece 10a secured to the upper end of a bailer 11. Note that top piece 10a of this embodiment is shaped differently than top piece 10 of FIG. 1, having a beveled annular shoulder 18a instead of flat annular shoulder 18. This figure also discloses external screwthreads 24a formed in cylindrical sidewalls 24 and complemental internal screwthreads 24b formed in closure means 40. The pitch of the screwthreads is steep so that closure means 40 is fully seated in four turns or less.

A bottom piece 10b is also provided at the lowermost end of bailer 11. Bottom piece 10b lacks mounting means 26 because bailers are lowered and lifted from their uppermost ends only. A second closure means 40 is employed to close the lowermost end of bailer 11 in the same way as a first closure means 40 is used to close the uppermost end thereof. First and second closure means 40 share a common size and configuration.

Elements 13 and 15 are a retainer and a check ball, respectively, and form no part of this invention, per se. Retainer 13 limits the travel of check ball 15 when liquid fluid enters the lowermost end of the bailer and lifts said check ball from its seat.

FIGS. 10–14 disclose a second embodiment of closure means 40. This second embodiment, denoted 40a, eliminates aperture 60, membrane 62, score lines 64, spout 70, and transverse plate 76.

Figure 11:
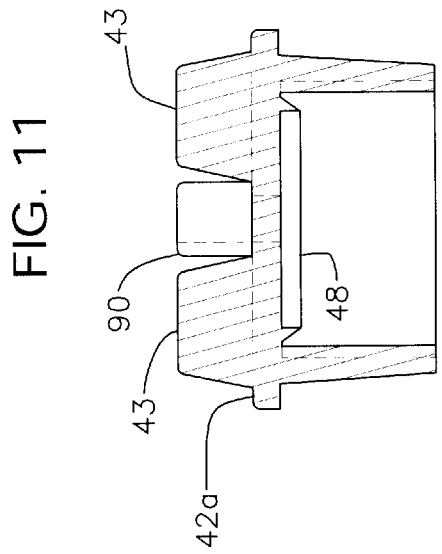
FIG. 11 is a sectional view taken along line 11—11 in FIG. 10.
Figure 10:
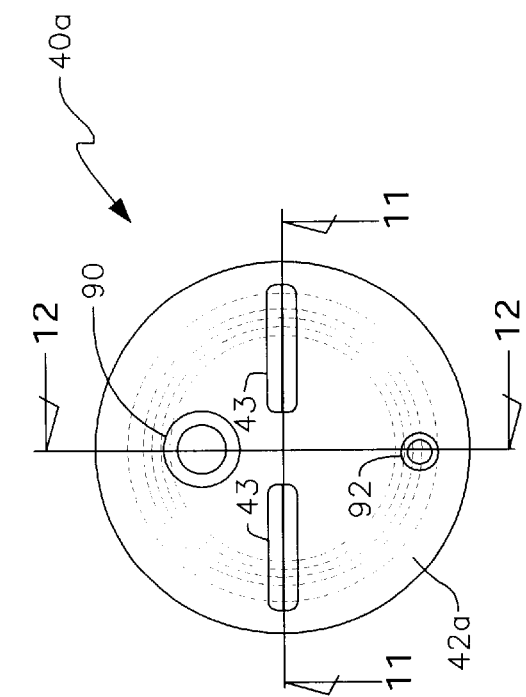
FIG. 10 is a top plan view of the closure means of the second embodiment.
Figure 12:
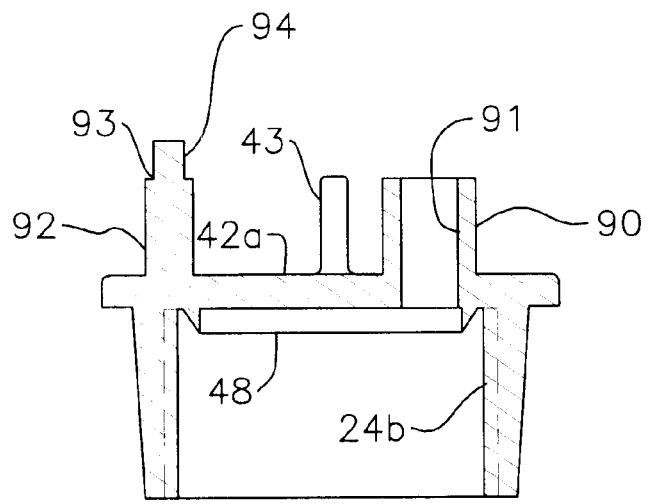
FIG. 12 is a sectional view taken along line 12—12 in FIG. 10.

As indicated in FIGS. 10–12, closure means 40a includes an upstanding tubular spout 90 formed in base 42a. Said spout is in open fluid communication with the hollow interior of the bailer and has inner cylindrical sidewalls 91. Liquid fluid within the bailer overflows spout 90 when the bailer is manually squeezed just prior to closure of the bailer.

Post 92 is formed in base 42a in diametric opposition to spout 90. Annular shoulder 93 formed therein reduces the diameter of its uppermost end 94 as best understood in connection with FIG. 12.

Figure 13:
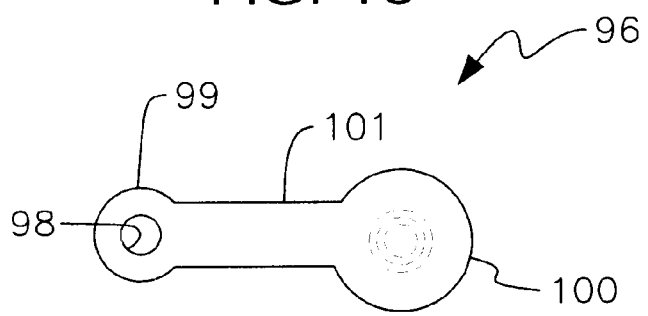
FIG. 13 is a top plan view of the elongate, flexible closure means of the second embodiment.
Figure 14:
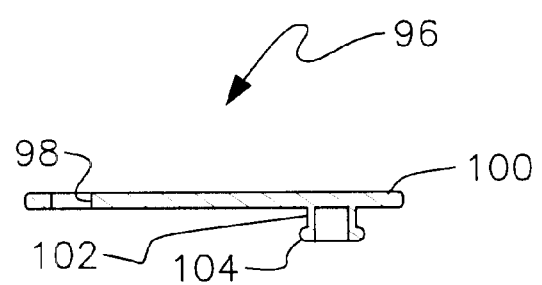
FIG. 14 is a longitudinal sectional view of said elongate, flexible closure means.

FIGS. 13 and 14 depict an elongate, flexible closure means 96 for sealing spout 90 after all air has been squeezed from the bailer. Closure means 96 has an aperture 98 formed in a first end 99 thereof. This aperture 98 tightly engages reduced diameter part 94 of post 92 so that closure means 96 is a permanent part of the bailer assembly and as such, unlike spout 70 of the first embodiment, is not subject to being lost or misplaced.

Free end 100 of closure means 96 is connected to first end 99 thereof by an elongate flexible neck 101. A cylindrical sealing means 102 depends from free end 100 and is disposed concentrically therewith as indicated in FIG. 13. A radially outwardly extending annular sealing bead 104 is formed in the distal free end of sealing means 102. Bead 104 tightly seals against inner cylindrical sidewalls 91 of spout 90 so that when the bailer is squeezed as aforesaid, sealing means 102 is inserted into spout 90 to prevent air from entering into the hollow interior of the bailer.

Since check ball 15 seals the lower end of bailer 11, it is necessary to invert the bailer so that check ball 15 is unseated from its valve seat. The bailer is then manually squeezed until liquid fluid within the bailer"s hollow interior overflows the flat rim of the bottom piece. A closure means 40 is then secured to said bottom piece and ambient air is prevented from entering into the bailer.

Both top piece 10a and bottom piece 10b, like top piece 10 of the first embodiment, terminate in a flat rim so that an associated closure means 40 fits squarely thereagainst to provide an air-tight seal.

This second embodiment eliminates the need to puncture a membrane formed in base 42 of closure member 40.

Flat guide members 43 are retained in this second embodiment of closure means 40, but they serve as finger holds to facilitate tightening and untightening of said closure means and not as guide means as in the first embodiment.

The second embodiment of the invention is not limited to the specific structure of elongate, flexible closure means 96. Alternative closure means may be found in U.S. Pat. No. 5,996,800 to the present inventor, entitled Resealable Plastic Bag Having Venting Means, for example. That patent is hereby incorporated into this disclosure by reference.

The bailer disclosed herein is the first bailer, anywhere in the world, that prevents contamination of a liquid fluid sample by oxygen and other gases from the ambient environment. Accordingly, when oxygen content tests are performed on the sample in a laboratory, the results will accurately measure the oxygen content of the liquid fluid as it existed in the well or other body of liquid fluid, uncontaminated by subsequent contact with ambient air.

Moreover, since both ends of the bailer are closed by the novel closure means 40, 40a disclosed herein, the long-established prior art practice of transferring the contents of a bailer to a separate container so that the container can be shipped to a laboratory is eliminated. This eliminates contamination of the liquid fluid by ambient air during the decanting procedure.

Instead, when both ends of the bailer have been sealed in the manner described above, i.e., after all air has been squeezed from the bailer and the opposite ends of the bailer tightly sealed with the novel closure means, the entire bailer is shipped to the laboratory. It can then be decanted in a sterile environment so that the contents of the bailer are not contaminated.

The bailer of this invention is therefore understood to be more than an air-tight bailer; it is a complete system for handling liquid fluids from the collection stage in the field through the transportation stage over the highways or through the air to the final delivery-to-the laboratory stage. As a complete system, it revolutionizes the art of environmental liquid fluid sampling.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,
What is claimed is:

1. A bailer, comprising:
a top piece adapted to engage a main body of said bailer;
said top piece having an open upper end of predetermined diameter;
a mounting member disposed in spanning relation to said open end of said top piece;
said mounting member adapted to be engaged by a rope means for lowering and lifting said bailer into and out of a body of liquid fluid;
a closure means for closing said open upper end when said bailer is substantially full of liquid fluid;
said closure means having a flat base that overlies said open upper end; and
said closure means having sidewalls depending from said flat base that are adapted to engage an external surface of said top piece;
whereby said closure means is secured to said top piece when said bailer is completely filled with said liquid fluid so that no air is trapped within said bailer.

2. The bailer of claim 1, further comprising:
said mounting members having a straight configuration; and
said mounting members being diametrically disposed across said open end.

3. The bailer of claim 1, further comprising:
said open upper end including a rim;
said mounting member disposed in slightly recessed relation to said open upper end of said top piece so that a predetermined extent of said open upper end extends beyond said recessed mounting members, said predetermined extent forming said rim and said disposition of said mounting member relative to said open upper end forming a recess.

4. The bailer of claim 3, further comprising:
a disc-shaped protuberance formed on an underside of said flat base;
said disc-shaped protuberance having a predetermined depth;
said disc-shaped protuberance having a diameter slightly less than an interior diameter of said sidewalls that depend from said base;
an annular groove circumscribing said disc-shaped protuberance;
said annular groove having a depth predetermined by said predetermined depth of said protuberance; and
said annular groove having a width predetermined by an internal diameter of said sidewalls that depend from said base and said diameter of said disc-shaped protuberance, said width of said annular groove being equal to a difference in diameters of said internal diameter of said sidewalls and said diameter of said disc-shaped protuberance.

5. The bailer of claim 4, further comprising:
said rim being substantially fully received within said annular groove when said closure means is disposed in closing relation to said open upper end; and
said recess being substantially fully occupied by said disc-shaped protuberance when said closure means is disposed in closing relation to said open upper end;
whereby leakage of liquid fluid from said bailer is substantially inhibited; and
whereby closing said open upper end with said closure means when said bailer is filled with liquid fluid substantially prevents ambient air from entering contacting said liquid fluid.

6. The bailer of claim 3, further comprising:
said closure means having a pair of guide plates formed integrally with a flat base wall and projecting upwardly therefrom.

7. The bailer of claim 6, further comprising:
each guide plate of said pair of guide plates having a flat structure and being positioned on a diameter of said base wall in diametrically opposed relation to one another.

8. The bailer of claim 7, further comprising:

a spout means having a leading end adapted for penetrating said flat base wall of said closure means;

said spout means having a trailing end adapted for connection with a hose means, said hose means being in fluid communication with a laboratory container adapted to receive said liquid fluid;

whereby liquid fluid within said bailer may flow through said spout means and through said hose means into said laboratory container when said leading end of said spout means penetrates said flat base wall.

9. The bailer of claim 8, further comprising:

a transverse plate of flat configuration mounted transversely to a longitudinal axis of said closure means;

a pair of slots formed in said transverse plate;

each slot of said pair of slots having its outermost end in open communication with an edge of said transverse plate;

each slot adapted to slidingly engage an associated closure means guide plate.

10. The bailer of claim 8, further comprising:

an opening formed in said flat base wall;

an imperforate membrane covering said opening so that no liquid fluid may flow through said opening;

said leading end of said spout means adapted to penetrate said membrane.

11. The bailer of claim 10, further comprising:

at least one score line formed in said membrane for weakening said membrane to facilitate its puncturing by said leading end of said spout means.

12. The bailer of claim 8, wherein said leading end of said spout has an approximately five degree draft formed therein.

13. A bailer, comprising:

a main body of cylindrical configuration;

a top piece having a lower end engaged to an upper end of said main body;

a flat rim formed by an upper end of said top piece;

a bottom piece having an upper end engaged to a lower end of said main body;

a flat rim formed by a lower end of said bottom piece;

a first closure means having a flat base that fits squarely against said flat rim of said top piece;

a second closure means having a flat base that fits squarely against said flat rim of said bottom piece;

said first and second closure means sharing a common size and configuration;

whereby ambient air is restricted from entering into a hollow interior when said hollow interior is filled with liquid fluid and said first and second closure means are secured to said top piece flat rim and said bottom piece flat rim, respectively.

14. The bailer of claim 13, wherein said first closure means further comprises:

a flat base;

cylindrical sidewalls depending from said base, said cylindrical sidewalls adapted to releasably engage said top piece;

an upstanding spout formed in said base;

an upstanding post formed in said base in diametrically opposed relation to said upstanding spout;

an elongate, flexible member having a first end and a second end connected to one another by a flexible neck;

said first end of said elongate flexible member being secured to said upstanding post;

said second end of said elongate flexible member being releasably secured to said upstanding spout in air-tight closing relation thereto;

whereby said second end of said elongate flexible member is secured to said upstanding spout after a filled bailer is squeezed until liquid fluid in a hollow interior of said bailer overflows said upstanding spout.

* * * * *